United States Patent
Elbaz et al.

(10) Patent No.: US 11,398,303 B2
(45) Date of Patent: Jul. 26, 2022

(54) CO-EXPRESSION SIGNATURES METHOD FOR QUANTIFICATION OF PHYSIOLOGICAL AND STRUCTURAL DATA

(71) Applicant: Northwestern University, Evanston, IL (US)

(72) Inventors: Mohammed S. M. Elbaz, Chicago, IL (US); Michael Markl, Chicago, IL (US)

(73) Assignee: Northwestern University, Evanston, IL (US)

( * ) Notice: Subject to any disclaimer, the term of this patent is extended or adjusted under 35 U.S.C. 154(b) by 147 days.

(21) Appl. No.: 17/004,779

(22) Filed: Aug. 27, 2020

(65) Prior Publication Data

US 2021/0065875 A1    Mar. 4, 2021

Related U.S. Application Data

(60) Provisional application No. 62/892,234, filed on Aug. 27, 2019.

(51) Int. Cl.
*G06T 7/10* (2017.01)
*G16H 30/00* (2018.01)
(Continued)

(52) U.S. Cl.
CPC ........... *G16H 30/00* (2018.01); *G06K 9/6215* (2013.01); *G06K 9/6298* (2013.01);
(Continued)

(58) Field of Classification Search
CPC .... G16H 30/00; G06K 9/6215; G06K 9/6298; G06T 2207/10088; G06T 2207/30104; G06T 7/10; G06T 7/0012
See application file for complete search history.

(56) References Cited

U.S. PATENT DOCUMENTS

| | | | |
|---|---|---|---|
| 7,700,293 B2* | 4/2010 | Chinnaiyan | C12Q 1/6886 435/6.14 |
| 8,103,076 B2* | 1/2012 | Larson | G06T 7/0016 600/363 |

(Continued)

OTHER PUBLICATIONS

Avants, Brian B et al. "A reproducible evaluation of ANTs similarity metric performance in brain image registration." NeuroImage vol. 54,3 (2011): 2033-44. doi:10.1016/j.neuroimage.2010.09.025 (Year: 2011).*

(Continued)

*Primary Examiner* — Shefali D Goradia
(74) *Attorney, Agent, or Firm* — Quarles & Brady LLP

(57) ABSTRACT

Described here are systems and methods for generating and analyzing co-expression signature data from scalar or multi-dimensional data fields contained in or otherwise derived from imaging data acquired with a medical imaging system. A similarity metric, such as an angular similarity metric, is computed between the data field components contained in pairs of voxels in the data field data. The data fields can be scalar fields, vector fields, tensor fields, or other higher-dimensional data fields. A probability distribution of these similarity metrics can be generated and used as co-expression signature data that indicate pairwise disparities in the data field data.

30 Claims, 6 Drawing Sheets

(51) Int. Cl.
*G06T 7/00* (2017.01)
*G06K 9/62* (2022.01)

(52) U.S. Cl.
CPC .............. *G06T 7/0012* (2013.01); *G06T 7/10* (2017.01); *G06T 2207/10088* (2013.01); *G06T 2207/30104* (2013.01)

(56) References Cited

U.S. PATENT DOCUMENTS

| | | | |
|---|---|---|---|
| 8,872,822 B2* | 10/2014 | Ekin | G06T 7/11 345/424 |
| 9,092,691 B1* | 7/2015 | Beaumont | G06T 7/0014 |
| 9,370,304 B2* | 6/2016 | Cao | G06T 7/0016 |
| 9,600,897 B2* | 3/2017 | Chandraker | H04N 5/147 |
| 2003/0084065 A1* | 5/2003 | Lin | G06F 16/58 |
| 2019/0125279 A1* | 5/2019 | Peikert | A61B 6/50 |

OTHER PUBLICATIONS

Rubner, Y. et al. "The earth mover's distance as a metric for image retrieval." International journal of computer vision 40.2 (2000): 99-121.

* cited by examiner

CO-EXPRESSION SIGNATURES METHOD FOR QUANTIFICATION OF PHYSIOLOGICAL AND STRUCTURAL DATA

CROSS-REFERENCE TO RELATED APPLICATIONS

This application claims the benefit of U.S. Provisional Patent Application Ser. No. 62/892,234, filed on Aug. 27, 2019, and entitled "CO-EXPRESSION SIGNATURES METHOD FOR QUANTIFICATION OF PHYSIOLOGICAL AND STRUCTURAL DATA," which is herein incorporated by reference in its entirety.

STATEMENT REGARDING FEDERALLY SPONSORED RESEARCH

This invention was made with government support under HL115828 awarded by the National Institutes of Health. The government has certain rights in the invention.

BACKGROUND

Several imaging modalities (e.g., MRI, PET, CT, echocardiography, ultrasound) can provide data information of pointwise distributed information over an organ or a structure of interest (e.g., heart, brain, breast, liver, kidney). The resulting data is comprehensive, but can be massive (e.g., thousands to millions of data points per patient) and include multi-dimensional and complex data fields (scalar fields, vector fields, tensor fields). Current methods for analyzing these data rely on simplifying the high dimensionality of the data into an approximate and much lower dimensional form, which by definition results in discarding a significant majority of the pointwise data information. As such, valuable patient information that can otherwise be useful or important for decision-making purposes is discarded when reducing the dimensionality of these data fields. Hence, no approach is currently available to utilize this data in its entire massive native high dimensional form for quantitative personalized assessment of patient's physiology and structure from imaging data.

SUMMARY OF THE DISCLOSURE

The present disclosure addresses the aforementioned drawbacks by providing systems and methods for generating data field co-expression signatures that use the entire data dimensionality of imaging data by encoding both local and global data associations over the full data dimensionality.

It is an aspect of the present disclosure to provide a method for generating co-expression signature data from data field data obtained from imaging data acquired with a medical imaging system. Data field data comprising a plurality of voxels are accessed with a computer system. The data field data were obtained from imaging data acquired from a subject using a medical imaging system. Each voxel in the data field data comprises a data field component, which may be a scalar field component, a vector field component, a tensor field component, or another suitable higher-dimensional data field component. Co-expression signature data are generated from the data field data by computing a similarity metric for each of a plurality of voxel pairs in the data field data and computing the co-expression signature data as a distribution of the similarity metrics. The similarity metric indicates one of a similarity or disparity between the data field component in each voxel pair, and the co-expression signature data encode the distribution of pairwise disparities or similarities in the data field data that are representative of at least one of physiological changes or structural changes in the subject.

It is another aspect of the present disclosure to provide a method for generating co-expression signature data from point-distributed data. The point-distributed data may be acquired with an imaging system, a biomedical measurement system, or other suitable measurement device that can acquire or generate data as point-distributed data. Point-distributed data comprising a plurality of data points are accessed, wherein each data point in the point-distributed data comprises an N-dimensional data field component. Co-expression signature data are computed from the point-distributed data by computing a similarity metric for each of a plurality of data point pairs in the point-distributed data and computing the co-expression signature data as a distribution of the similarity metrics. The similarity metric indicates one of a similarity or disparity between the N-dimensional data field component in each data point pair. The generated co-expression signature data encode the distribution of pairwise similarities or disparities in the point-distributed data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
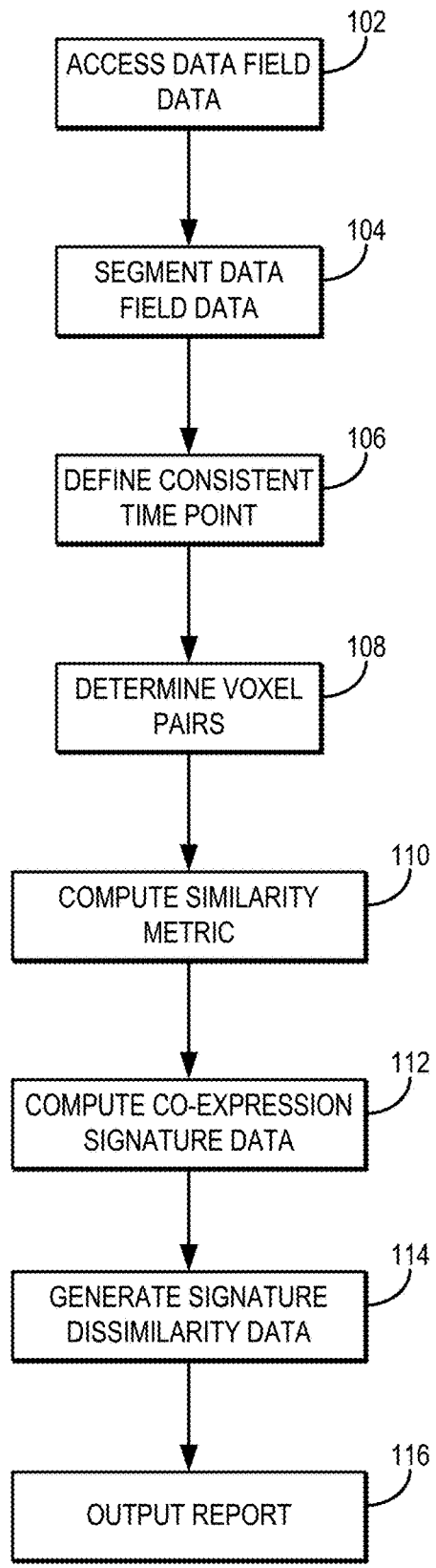
FIG. 1 shows a flowchart for a process for generating and analyzing co-expression signature data from data field data obtained from imaging data acquired with an imaging system, such as a medical imaging system.

Described here are systems and methods for generating and analyzing co-expression signature data from data fields contained in or otherwise derived from point-distributed data while exploiting the entire data dimensionality of the data fields contained in or derived from the point-distributed data. The point-distributed data may include imaging data (e.g., medical imaging data) acquired with an imaging system (e.g., a medical imaging system), biomedical measurement data (e.g., electrophysiology data, voltage maps) acquired with a biomedical measurement system (e.g., electrophysiology recording electrodes), or other suitable imaging or data acquisition systems capable of acquiring data as point-distributed data.

The co-expression signature data generally indicate pairwise similarities or disparities between pairs of data points (e.g., voxels or other N-dimensional data points) in the data field. As one example, the co-expression signature data can be physiological co-expression signature data that represent pairwise similarities or disparities in physiological-based data fields (e.g., cardiovascular and neurovascular blood flow, functional activity). As another example, the co-expression signature data can be structural co-expression signature data that represent pairwise similarities or disparities in structural-based data fields (e.g., extracellular volumes, tumor composition, infarction structure, thrombus formation, structural deformations). These co-expression signature data permit identifying precisely personalized biomarkers in various diseases throughout the body.

The systems and methods described in the present disclosure provide quantitative methods for analyzing data fields or other point cloud or point-distributed data contained in or otherwise derived from medical imaging or other suitable data, generating output as co-expression signature data that indicate a pairwise similarity between pairs of voxels in the data fields. The processing can be automated, enabling fast and reproducible analysis of large patient cohorts. Advantageously, these techniques exploit the entire data dimensionality of the data field and are scalable to any data dimension (e.g., 1D, 2D, . . . , ND for positive integer values of N). The data field can be any type, including scalar fields, vector fields, tensor fields, matrices, and so on. Both local and global data field distributions can be encoded, enabling precise evaluation.

Using the systems and methods described in the present disclosure, unique, personalized, data-driven signatures of anomalies can be generated from data fields contained or otherwise derived from one or more types of data, which may be imaging data, medical imaging data, or other suitable point-distributed data. Moreover, standardized quantitative comparisons can be made among different subjects, patient populations, and so on. In this way, precision medicine techniques can be implemented by assessing patient health using personalized patient data physiology and/or structural co-expression signatures compared against other individual patients.

The output co-expression signature data can be used to generate fusion of data from different imaging modalities for robust multi-modality assessments. Additionally or alternatively, the output co-expression signature data enables natural quantification or data fusion between data from different imaging scales (e.g., macroscale, microscale, nanoscale). As an example, macroscale imaging may refer to imaging modalities such as MRI, CT, and other such imaging modalities and techniques that generate images with a spatial resolution capable of resolving features at a macroscopic level; microscale imaging may refer to imaging modalities such as histology microscopic images, optical coherence tomography ("OCT"), and other such imaging modalities and techniques that generate images with a spatial resolution capable of resolving features at a microscopic level; and nanoscale imaging may refer to imaging modalities such as optical imaging, microscopy, and other such imaging modalities and techniques that generate images with a spatial resolution capable of resolving features at the nanoscale.

The co-expression signature data are insensitive to noise and minor data uncertainties, thereby allowing for robust standardized quantitative comparisons of large, comprehensive, amounts of imaging data among different patients. Furthermore, as noted above, data from different imaging modalities, among different imaging protocols using the same imaging modality (e.g. that measure different functional, structural, and/or physiological data), and/or among different image sources can be naturally fused or compared using co-expression signature data, thereby enabling intrinsic patient assessment amongst these various different images without the need for complex, error-prone data registration/alignment techniques. As one non-limiting example, co-expression signature data can be generated from flow data (e.g., 4D flow MRI vector field data) in order to quantify aortic blood flow abnormalities. Such flow data includes 7-dimensional data field data, corresponding to three spatial dimensions, one temporal dimension, and three directional velocity components. In other implementations, co-expression signature data can be generated from data field data associated with other anatomical regions (e.g., heart, brain, lungs, kidneys, peripheral vasculature, other vasculature, cellular regions, and so on) from any imaging modality that provides point-distributed data field and at any data dimension.

Thus, the systems and methods described in the present disclosure can be applied to a variety of clinical and imaging applications, including cardiovascular applications, neurovascular applications, and oncology-based applications.

As an example, cardiovascular applications can include deriving and/or assessing structural co-expression signatures of tissue damage (e.g., after myocardial infarction, thrombosis) from MRI-T1 mapping. As another example, cardiovascular applications can include deriving and/or assessing physiological signatures of cardiac and vascular blood flow (e.g., from 2D color Doppler Echocardiography or 4D Flow MRI), as in patients with congenital heart disease, pulmonary hypertension of heart valve disease, patients with heart transplantation, and so on. As still another example of cardiovascular applications, functional signatures of heart contractility can be derived and/or assessed (e.g., from cardiac CT, MR tissue phase mapping, cine MRI, echocardiography, or diffusion-weighted imaging). All such co-expression signatures enable quantitative standardized comparison among different patients and healthy controls, or patients with different degrees of the cardiovascular disease under study.

As another example, neurovascular applications can include deriving and/or assessing physiological signatures of brain tumor from MRI, PET, or SPECT data. As another example neurovascular applications can include deriving and/or assessing structural co-expression signatures of brain tissue damage (e.g., after stroke) from MRI data, CT data, or both. As still another example, neurovascular applications can include deriving and/or assessing neurovascular blood flow activity (e.g., from 4D flow MRI). In other implementations, neurovascular applications can include deriving and/or assessing brain connectivity from diffusion tensor data fields generated from diffusion tensor imaging (DTI) data (e.g., after stroke or brain damage). In still other implementations, neurovascular applications can include deriving and/or assessing brain functional activity (e.g., by deriving signatures from fMRI data).

As still another example, oncology applications can include deriving and/or assessing quantitative structural signatures to assess tumor structure, composition, heterogeneity, or combination thereof, from PET data, SPECT data, or both. As another example, oncology applications can include deriving and/or assessing physiological signatures (e.g., cardiac function, blood flow) from MRI data, CT data, or both, in order to assess the impact of tumor on a subject's physiology. As still another example, oncology applications can include deriving and/or assessing fused structural-functional signatures of brain tumor by combining co-expression signature data generated from PET or SPECT data with co-expression signature data generated from MRI data, CT data, or both.

As noted above, in some applications the systems and methods described in the present disclosure can be used in connection with data fields contained in or derived from optical imaging. As an example, optical imaging such as OCT can be used to identify vulnerable coronary plaque associated with coronary heart disease. PCT can also be used for retina imaging, such as for assessing the surface of the retina. The spatial resolution of OCT is typically on the order of micrometers and, therefore, can provide high resolution imaging. OCT data are most commonly 2D, 3D, or 4D data.

In still other examples, the systems and methods described in the present disclosure can be used in connection with data field data that are contained in or derived from other measurement devices, such as electrophysiology devices. As an example, electrophysiology data (e.g., point-distributed voltage maps, point-distributed activation maps) can be derived from intracardiac catheter-based measurements. These data can be analyzed to identify scar tissue regions in patients with atrial fibrillation, tachycardia, or other cardiac electrical disorder. Based on such analyses, guidance can be provided for treatment, such as guidance for an ablation procedure.

The systems and methods described in the present disclosure can also be used for post-treatment and/or post-surgery evaluation. For instance, by comparing the subject's personalized co-expression signatures before and after treatment and/or surgery (or over multiple follow-ups), the efficacy of that treatment and/or surgery can be assessed or monitored. For example, the physiological and/or structural co-expression signature data can be monitored to evaluate whether they are getting closer to normal after treatment and/or surgery, where a return to normal is indicative of an efficacious treatment and/or surgery.

As noted above, co-expression signature data can be generated from data field data contained in or otherwise derived from imaging data acquired with different imaging modalities. In these instances, the co-expression signature data generated from these different imaging modalities can be fused or otherwise compared. As an example, structural co-expression signature data from MRI data and/or CT data can be used with tissue metabolic activity from PET. As another example, flow data from MRI can be combined with high resolution structural information from CT. As still another example, point-distributed data from histology or microscopic images (e.g., histological images of a tumor) can be fused with one or more different image types or imaging modalities.

Advantageously, the co-expression signature data generated using the systems and methods described in the present disclosure can be used as training data or input data for machine learning algorithms. For instance, the co-expression signature data can provide "blue prints" for different disease states. By training machine learning algorithms using example co-expression signatures with corresponding labels (e.g., degree of disease vs. associated co-expression signature), one or more machine learning algorithms can be trained to automatically predict and/or identify the disease corresponding to each physiological/structural co-expression signature from new incoming patient data.

Referring now to FIG. 1, a process for generating and analyzing co-expression signature data from data fields contained in or otherwise derived from imaging data acquired with an imaging system is shown. Generally, the process can generate the co-expression signature data for a subject based on the data fields contained in or otherwise derived from the imaging data, which may be referred to as data field data. The co-expression signature data can then be used to generate reports, which may include distribution graphs (e.g., probability distribution graphs). A subject's co-expression signature data can also be output to a practitioner and/or compared to baseline data such as historical data of the subject and/or a data from a database of other subjects. Comparing the subject co-expression signature data to baseline data can provide a standardized personalized subject assessment of physiological and structural data for a comprehensive precise assessment of subject health.

At 102, the process can access data field data, which may include a plurality of voxels corresponding to an anatomical region, which may correspond to a volume or regions of interest in a subject. The data field data can include data fields contained in or otherwise derived from imaging data acquired from the subject using an imaging system. Examples of data fields include vector fields (e.g., color Doppler velocity, 4D flow three-directional velocity vectors), tensor fields (e.g., diffusion tensors computed based on diffusion tensor imaging), or scalar fields (e.g., CT images, PET images, MRI, T1 maps, T2 maps, activation maps generated based on fMRI, angiography). As one non-limiting example, the anatomical region can contain one or more blood vessels, such as an aorta of the heart. In these instances, the data field data can include flow data indicative of a flow vector field.

As indicated above, the data field data can be contained in or otherwise derived from imaging data acquired with any number of different imaging modalities. For instance, the data field data can be obtained from imaging data acquired from a subject using an imaging system such as a magnetic resonance imaging (MRI) system; a computed tomography (CT) system; an echocardiography or other ultrasound system; a positron emission tomography (PET) system; optical imaging, such as OCT, microscopy, histological imaging, and so on; or other imaging or biomedical measurement systems that produce a pointwise distributed data field. Each voxel in the data field data can represent an entry in the data field (e.g., a scalar value, a vector, a tensor). As one non-limiting example, where the data field data are vector field data, each voxel can include flow vector data (e.g., three directional velocity components) and can be associated with a time value and/or one or more spatial location values, such as three dimensional values (e.g., x, y, and z values). It is appreciated that each voxel could include one or more directional velocity components. In general, the data field data can include voxels acquired at different time points, which can capture the anatomical region at different points in a biological process cycle. For example, the data field data can include voxels sensed at various time points over a cardiac cycle. The process can then proceed to 104.

At 104, the process can segment the data field data to generate a segmented volume from the anatomical region. The segmented volume may in some instances be a segmented vessel volume that correspond to one or more blood vessels that have been segmented from the anatomical region. For example, the process can segment an aorta from the anatomical region. In general, the voxels in the segmented volume include voxels corresponding to the volume of segmented anatomy, such as one or more segmented blood vessels. In this way, the segmented volume can enable localized processing of the data field data over a volume of interest within the anatomical region. Alternatively, the data field data in the entire anatomical region can be processed without segmenting out a segmented volume. The process can then proceed to 106.

At 106, the process can define a consistent time point or range of time points in the biological process cycle at which to derive co-expression signature data from the data field data. For example, the process can define the consistent time point to be a time value corresponding to a point in the subject's cardiac cycle. As one non-limiting example, the consistent time point can correspond to a peak (e.g., an R peak of the QRS complex) in a portion of the cardiac cycle. The peak can be determined using methods known in the art. As will be explained below, choosing a consistent time point allows the co-expression signature data to be compared to baseline data. As another example, the process can define a range of time points, such as a range of time points over diastole, a range of time points over systole, or a range of time points over the entire cardiac cycle. The time point or range of time points can also be defined relative to a biological process cycle other than the cardiac cycle. For instance, the time point or range of time points may be defined relative to a respiratory cycle. The process can then proceed to 108.

At 108, the process can determine a plurality of voxel pairs based on the data field data. Each pair of voxels can include voxels associated with different spatial or temporal location values. The selected pairs may constitute the entire data field, or a subset of the data field. In some embodiments, the pairs can be determined using a random sampling technique. For instance, the voxel pairs can be determined using a stochastic discrete uniform random sampling of a predetermined number of voxel pairs over the entire segmented volume or anatomical region. In a non-limiting example, the predetermined number of voxel pairs can includes upwards of three million pairs for a segmented vessel volume corresponding to an aorta.

As noted above, in some instances data from among different imaging modalities or protocols can be fused or otherwise integrated. As one non-limiting example, physiological data can be fused or otherwise integrated with structural data. As another non-limiting example, flow data from MRI data can be fused or otherwise integrated with structural data from CT, ultrasound, or histological data. In these instances, the voxel pair can be composed from two different modalities or imaging sources (i.e., each pair can be composed of one voxel/point data field from a first image source and the other voxel/point data field from a second image source). Similarly, the source of these voxel/point pairs can be from two different scales. As one non-limiting example, each pair can be composed of one voxel/point data field from a first image source at a first scale (e.g., a macroscale voxel from MRI) and the other voxel/point data field can be from a second image source at a second scale (e.g., a microscale voxel from OCT or histological data). In this way, a natural quantitative method for integrating different imaging data from different modalities or imaging sources is provided without the need for complex, error-prone pre-alignment/registration to permit such integration. The process can then proceed to 110.

At 110, the process can compute a similarity metric for each of a plurality of voxel pairs in the data field data. The similarity metric can be an angular similarity metric that can indicate a similarity between an angle of the data field data entry in each voxel pair included in the plurality of voxel pairs. For instance, the angular similarity metric can be a measure of similarity of the orientation of flow vector data between two voxels. In other instances, the angular similarity metric can be a measure of similarity between one or more angles between tensor data contained in the pair of voxels. In some embodiments, the angular similarity metric θ can be calculated as, $$\theta_i = \arccos\left(\mathrm{dot}\left(\frac{V_A}{|V_A|}, \frac{V_B}{|V_B|}\right)\right), i = 1...N \quad (1)$$

where $V_A$ is flow vector data included in a first voxel included in a given voxel pair and $V_B$ is flow vector data included in a second voxel included in the given voxel pair, dot( . . . ) is a dot product function, i is the index of a given voxel pair, and N is the total number of voxel pairs. Using the angular similarity metric enables summarizing the relationship between voxels using a single value, and can also make comparisons between subjects easier. Advantageously, the angular relationship between data field entries (e.g., vectors, tensors) may be more significant than the length (i.e., magnitude) of each component for determining subject medical conditions. Additionally, different imaging techniques or imaging modalities might generate different data field component lengths for a given voxel, but should generate the same angle for the voxel. Thus, by computing an angular similarity metric comparisons across different imaging techniques and imaging modalities can be possible.

In some embodiments, a similarity metric other than an angular similarity metric can be calculated. For example, a pair-wise relative velocity disparity magnitude can be calculated based on the magnitude of the difference in each directional flow velocity included in the voxel. For instance, the relative velocity disparity can be as an L-norm of ($V_A$-$V_B$), where $V_A$ and $V_B$ are pairwise velocity vector fields (e.g., from 4D flow MRI) or scalar velocity fields (e.g., from echo Doppler). The pair-wise relative velocity disparity magnitude can then be used in place of the angular velocity metric in subsequent steps.

Additionally or alternatively, the similarity metric may be an L-norm or a matrix norm. In general, L-norms can include an L0-norm, an L1-norm, an L2-norm, a Frobenius norm, a max norm, or other suitable norm. The norm metrics can be normalized or non-normalized. Such similarity metrics can be advantageous for applications where the magnitude information in the voxel pair is important. As a non-limiting example, for scalar data fields (e.g., CT data, PET data, ultrasound data, T1 maps), the similarity metric can be the L-norm.

As another non-limiting example, for tensor field data (e.g., DTI), the similarity metric can be a matrix norm. In these instances, each data point in the data field data can include a tensor, which can be represented as an N×N or N×M matrix, such that the pairwise similarity metrics will be computed between such matrices. In general, the matrix norm may be a p-norm, entrywise matrix norms, Schatten norms, or so on. Alternatively, the similarity metric can be a cross-correlation or covariance metric between these pairwise matrices.

After the similarity metric has been calculated for each voxel pair in the plurality of voxel pairs, the process can proceed to 112.

Figure 2:
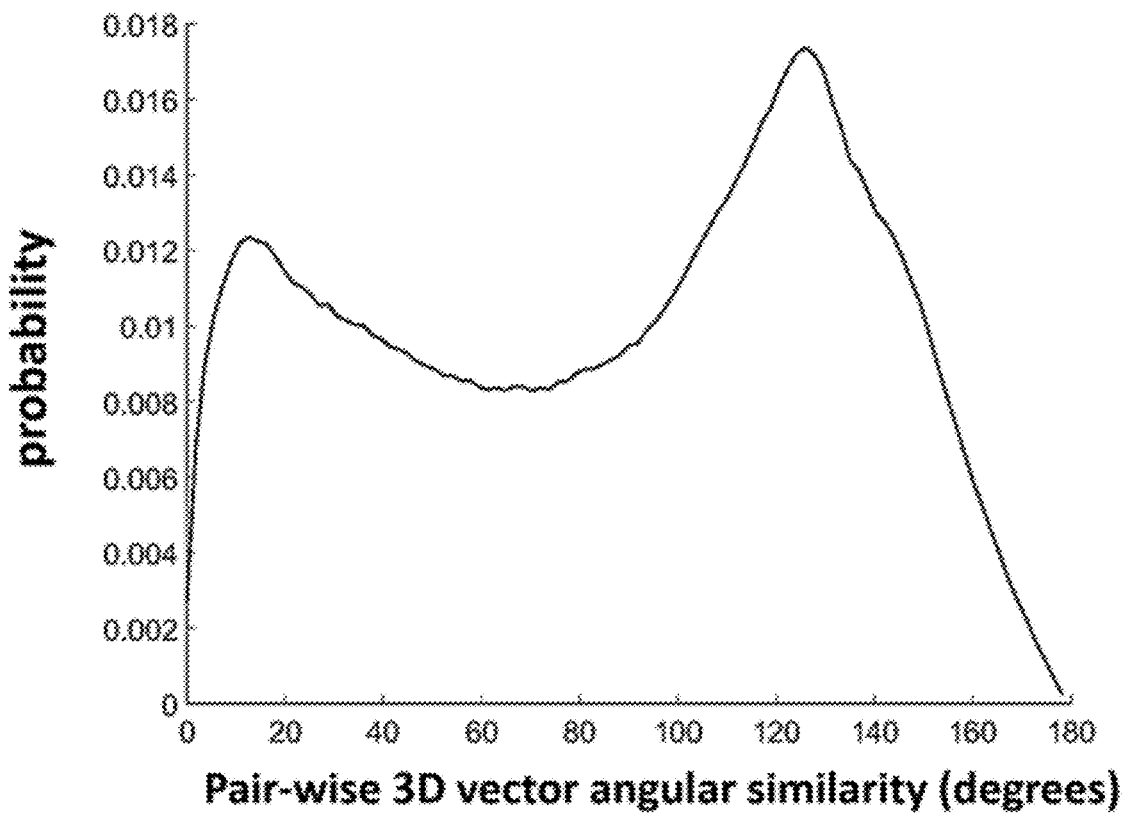
FIG. 2 shows an exemplary graph of probability density of angular similarity for an exemplary co-expression signature.
Figure 3:
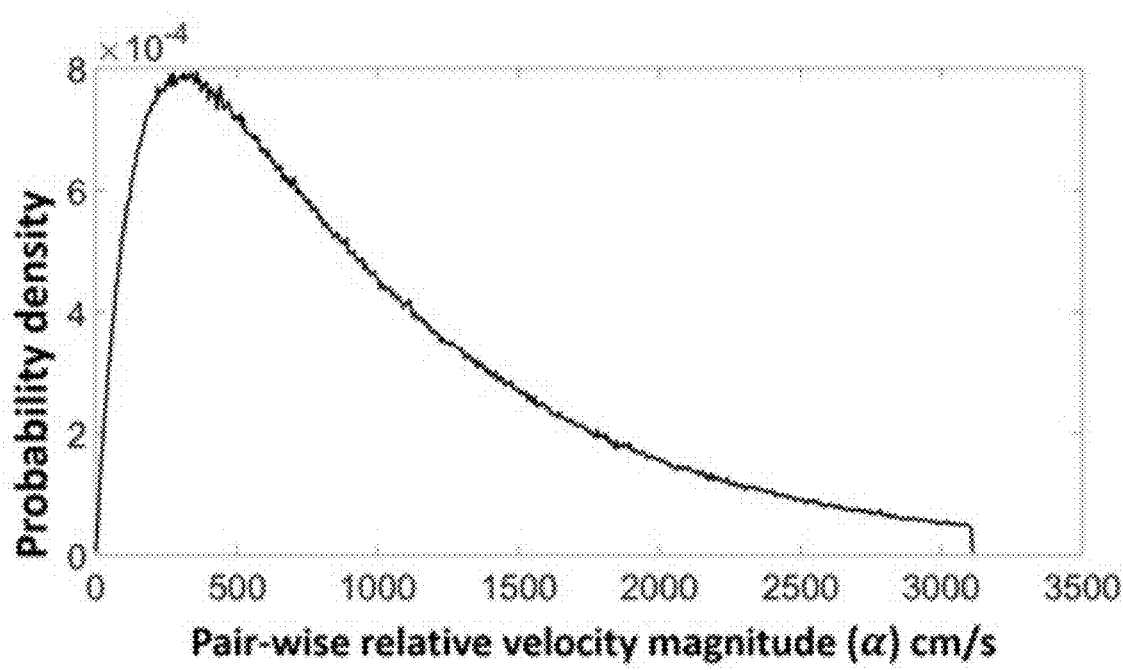
FIG. 3 shows an exemplary graph of probability of pair-wise relative velocity disparity magnitude.

At 112, the process can compute co-expression signature data as a distribution of the similarity metrics. The distribution may be a probability density function, a cumulative density function, another suitable probability distribution, a normalized histogram, a non-normalized histogram, or so on. The co-expression signature data can indicate pairwise disparities in the data field data that are representative of physiological changes, structural changes, or both, in the subject. In some embodiments, the co-expression signature data S can be computed using equation (2) below:

$$S = \text{histogram}(\theta, B) \quad (2)$$

where $\theta$ is the angular, or other, similarity metric, B is a predetermined number of bins, and histogram( . . . ) is a histogram generating function. The co-expression signature data S can summarize the differences (e.g., angular differences of five degrees, ten degrees, and so on) in voxel pairs of the data fields, and how likely each difference is. In one non-limiting example, B was selected as one hundred and eighty bins; however, it will be appreciated that other values can be used. Briefly referring to FIG. 2, an example of a graph showing the probability of angular similarity for an example co-expression signature computed using equation (2) is shown. Briefly referring to FIG. 3, an example of a graph showing the probability of pair-wise relative velocity disparity magnitude is shown. The process can then proceed to 114.

At 114, the process can generate signature dissimilarity data by comparing the co-expression signature data with baseline data. The baseline data can include co-expression signature data for one or more healthy control subjects, co-expression signature data for a particular population (e.g., a population average), historical co-expression data for the subject, or other examples of co-expression signature data that can be used as a baseline for comparison. In some embodiments, the baseline data can include co-expression signature data from other subjects without a particular disorder (e.g., bicuspid aortic valve (BAV) disease), such that the baseline data are representative of a "healthy" population to which a subject can be compared in order to determine a risk level for the given disorder. In some embodiments, the baseline data can include co-expression signature data corresponding to historical data for the subject. The subject historical data can be used to track a trend of the subject over time. For instance, when the baseline data include historical co-expression signature data for the subject, the dissimilarity data can be used to monitor changes (positive or negative) in the subject, which may include monitoring or otherwise assessing the efficacy of a treatment being administered to the subject.

As one example, baseline signature dissimilarity values $D_{cntrl}$ for the baseline data can be computed as, $$D_{cntrl_i} = \Sigma_{n=1}^{N_{cntrl}} EMD(S_i, S_n), \ i=1 \ldots N_{cntrl} \quad (3)$$

where $N_{cntrl}$ is the number data sets (e.g., number of subjects, number of historical co-expression signature data sets) included in the baseline data; $S_i$ and $S_n$ are co-expression signature data for subjects included in the baseline data; and EMD( . . . ) is an earth mover's distance function. It is appreciated that distance metrics other than an earth mover's distance can be used to compare co-expression signature data for a given entry included in the baseline data ($S_i$) against other all other entries included in the baseline signature data ($S_n$, n=1 . . . $N_{cntrl}$, i≠n). For example, the distance metric may be a distribution distance metric, such as a Chi-squared distribution distance, a Mahalanobis distance, an L-norm distance, a cosine distance, a Kolmogorov distance, a total variation distance, a Mallow's distance, a Bhattacharyya distance, a Bellinger distance, a Bregman divergence, a Kullback-Leibler divergence, and so on. The baseline signature dissimilarity values $D_{cntrl}$ can give a general overview of how functionality of portions of an organ such as an aorta varies in a healthy population.

As another example, the dissimilarity data can be computed by comparing the co-expression data with baseline data, as noted above. In these instances, the co-expression signature data calculated at step 112 can be referred to as $S_k$ and compared to the baseline as, $$D_k = \Sigma_{z=1}^{N_{cntrl}} EMD(S_k, S_z) \quad (4)$$

where $S_k$ is the co-expression signature data of the given subject, $N_{cntrl}$ is the number of subjects (or other data sets or entries) included in the baseline data, EMD( . . . ), is an earth mover's distance function, and $S_z$ is co-expression signature data corresponding to an entry, z, in the baseline data. As noted above, it will be appreciated that distance metrics other than an Earth Mother's Distance can also be used, including Wasserstein distance metrics. The process can then proceed to 116.

At 116, the process can output a report based on the similarity metric (e.g., an angular similarity metric $\theta$), the co-expression signature data $S_k$, the baseline signature dissimilarity values $D_{cntrl}$, and/or the co-expression signature dissimilarity data $D_k$ to a memory and/or a display. The report can include graphs, charts, or other visual aids generated based on the similarity metric (e.g., an angular similarity metric $\theta$), the co-expression signature data $S_k$, the baseline signature dissimilarity values $D_{cntrl}$, and/or the co-expression signature dissimilarity data $D_k$. The report can include the values (in other words, the "raw data values") of the similarity metric (e.g., an angular similarity metric $\theta$), the co-expression signature data $S_k$, the baseline signature dissimilarity values $D_{cntrl}$, and/or the co-expression signature dissimilarity data $D_k$.

It is appreciated that the process can be applied to various data field information types regardless of complexity level (scalar, vectors, tensors, etc.) and can be scaled to any data dimension (1D, 2D, . . . , N-D), can be applied to any imaging modality that produces flow or other data as point-wise distributed data fields. Therefore, the process can be used to generate standardized personalized patient assessment of physiological and structural data for a comprehensive precise assessment of patient health.

Figure 4A:
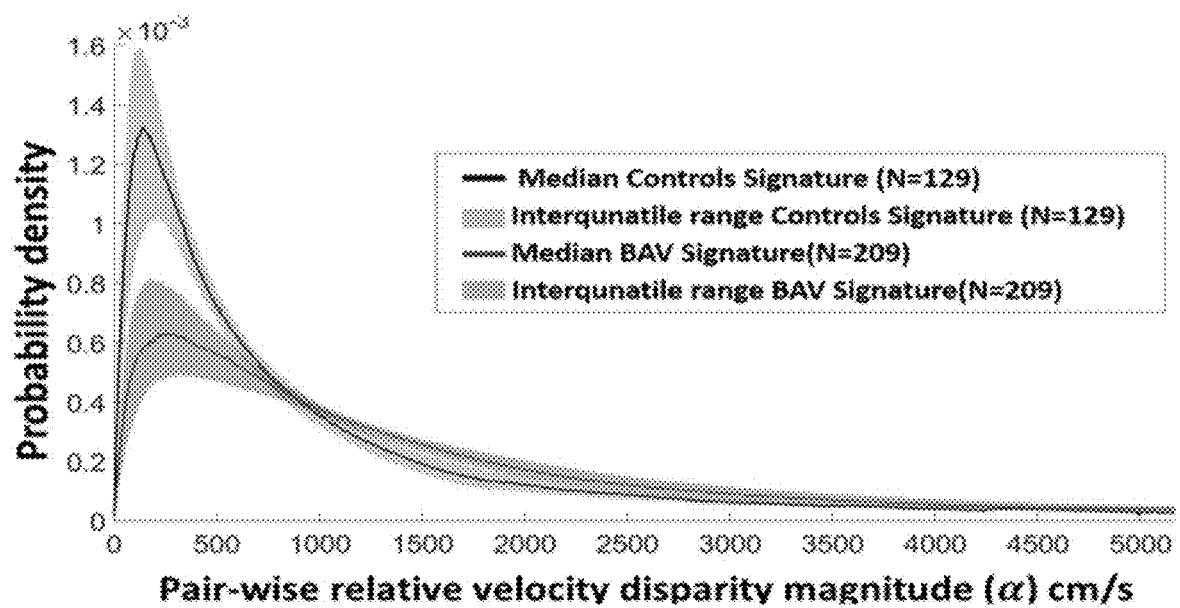
FIG. 4A shows a probability density graph for pair-wise relative velocity disparity magnitude for a control group of patients corresponding to baseline data and a group of bicuspid aortic valve (BAV) disease patients.

Referring to FIG. 4A, a probability density graph for pair-wise relative velocity disparity magnitude for a control group of patients corresponding to baseline data and a group of BAV disease patients is shown. The pair-wise relative velocity disparity magnitude was calculated for each subject in the control group and the BAV disease group, and the median and interquartile ranges were plotted at each bin value. As can be seen, the control group presented consistent hemodynamic signatures while BAV patients showed distinctly altered hemodynamic co-expression signatures (probability density functions), characterized by elevated velocity disparity (i.e., lower probability density for small disparity values and the wider probability density function for the higher disparity values).

Figure 4B:
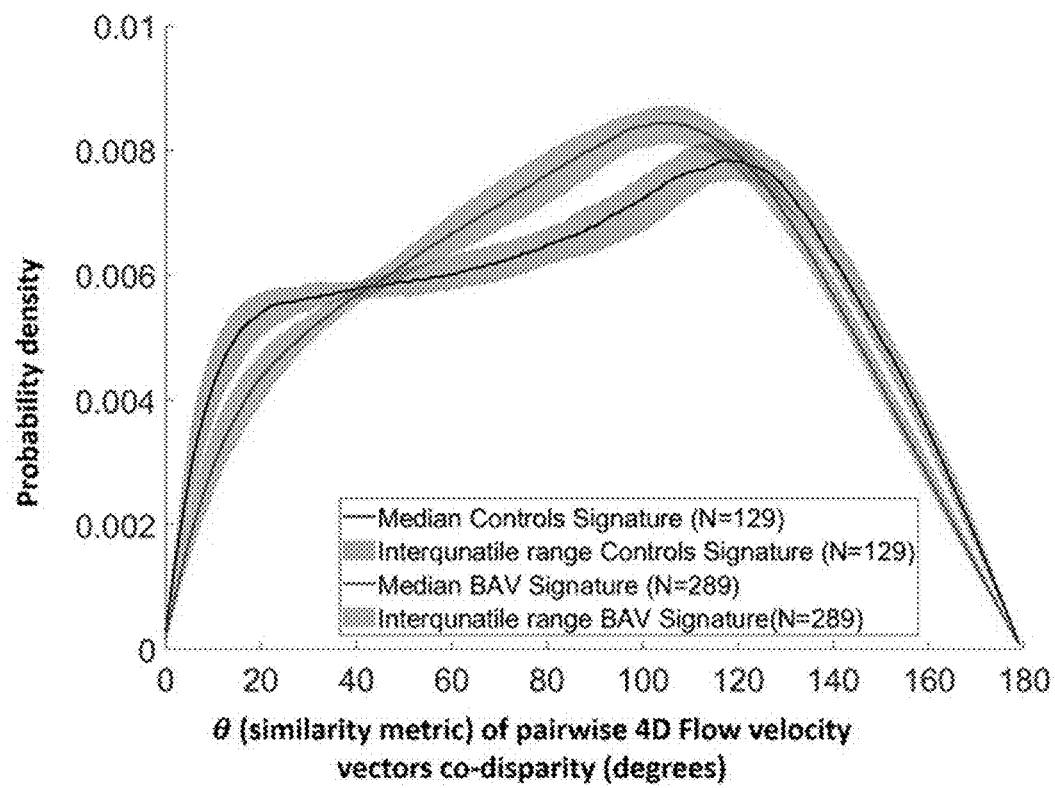
FIG. 4B shows a probability density graph for pair-wise velocity vector co-disparity (degrees) for a control group of patients corresponding to baseline data and a group of bicuspid aortic valve (BAV) disease patients.

Referring to FIG. 4B, a probability density graph for similarity metrics of pairwise 4D flow velocity vectors co-disparity for a control group of patients corresponding to baseline data and a group of BAV disease patients is shown. In this example study, healthy controls showed consistent 4D flow signature profiles that were distinctly altered in BAV. Patient signatures highlighted increased velocity co-disparities (i.e., higher density of large theta values (mismatch) and lower density of smaller theta values (match)).

As described above, in this example study co-expression signatures were constructed as the probability distribution of the pairwise angular similarity function estimated by a normalized histogram. The signature dissimilarity comparison was then performed by first computing an EMD of the probability distributions as the dissimilarity metric to compare the co-expression signatures. Baseline signature dissimilarity values were established by comparing each control's signature to all other controls using EMD. For each control, a cumulative dissimilarity index, Dcntri, was then computed as the sum of its EMD dissimilarity to all other controls. For each BAV patient, a cumulative dissimilarity index, Dmv, was computed as the sum of its dissimilarities against all controls' signatures.

The results shown in FIG. 4B are derived from 4D flow signatures of 289 BAV patients versus 129 healthy controls (measured over entire systole). Compared to controls, patients showed higher co-disparity/mismatch in the flow dynamics over systole indicated by higher density of large theta values (mismatching velocity vectors) and lower density of the low theta values (matching velocities). Note that signature area under the curve is standardized to 1 by definition enabling systematic comparison among subjects.

Figure 5A:
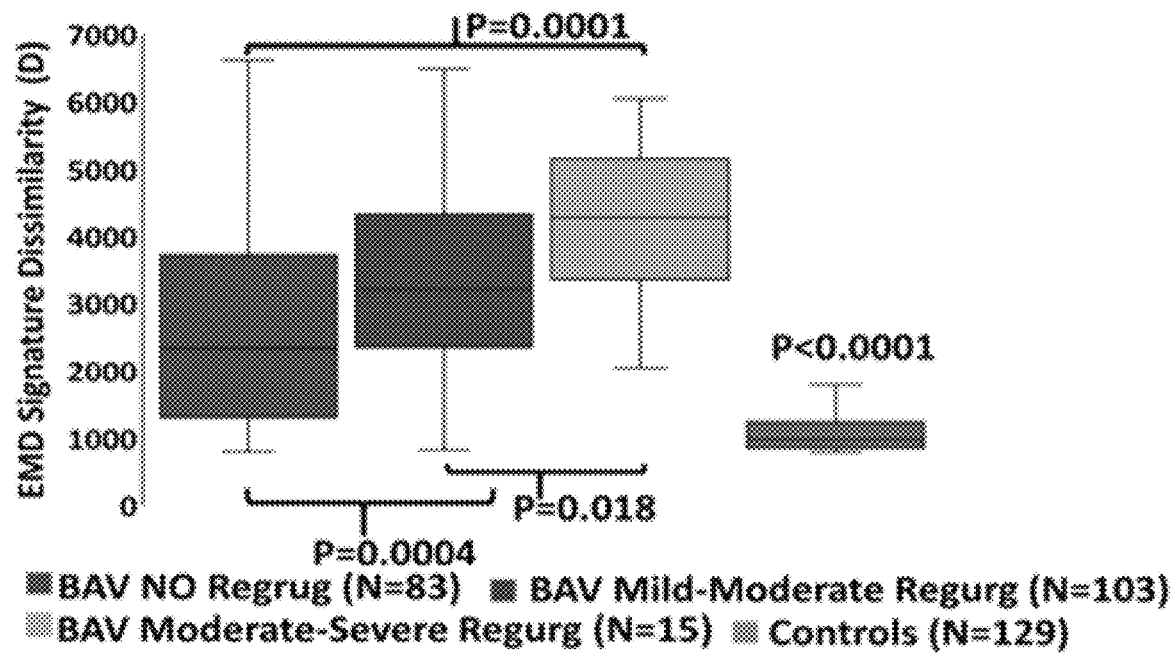
FIG. 5A shows a box plot of a cumulative earth mover's distance (EMD) dissimilarity index between the co-expression signature of BAV patients with different degrees of regurgitation & vs. control patients.
Figure 5B:
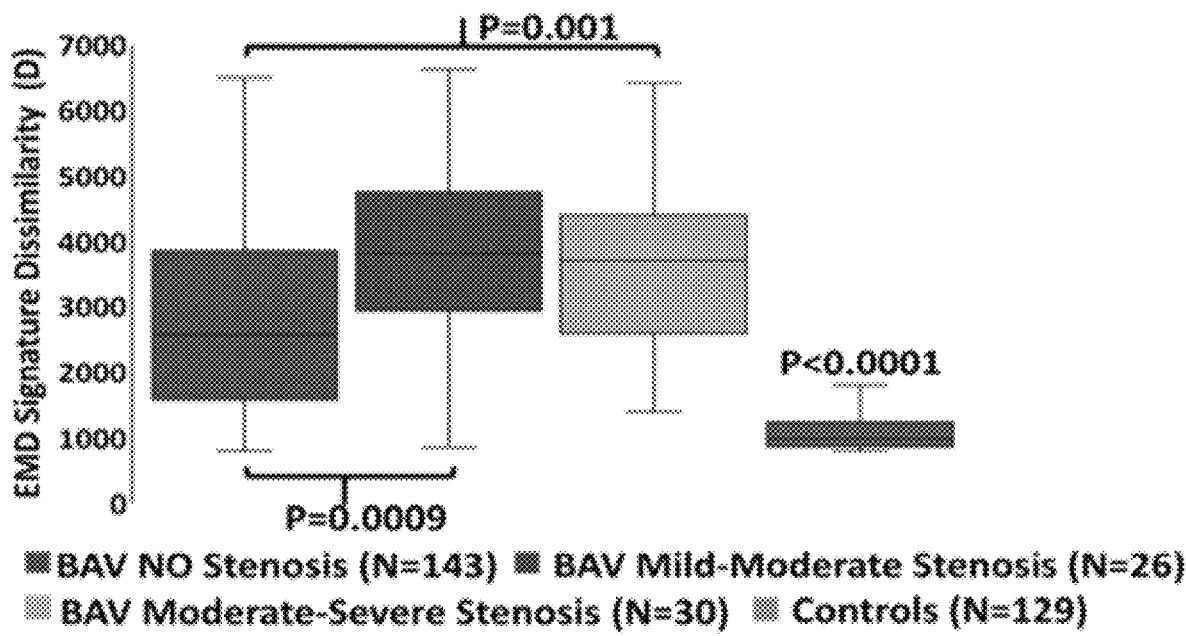
FIG. 5B shows a box plot of the cumulative EMD dissimilarity index of BAV patients with different degrees of stenosis & vs. control group patients.

Referring to FIG. 5A, a box plot of the cumulative EMD dissimilarity index (D) of BAV patients with different degrees of regurgitation & vs. control patients is shown. Referring to FIG. 5B, a box plot of the cumulative EMD dissimilarity index (D) of BAV patients with different degrees of stenosis & vs. control group patients is shown. FIGS. 3A and 3B show significant differences in cumulative dissimilarity indices (D) between BAV patients with different aortic valve stenosis and aortic valve regurgitation severity and compared to control group patients.

The findings shown in FIGS. 4, 5A, and 5B demonstrate the feasibility of a novel 4D hemodynamic signature concept to identify distinctly altered volumetric hemodynamics in the aorta of BAV patients and discriminate different degrees of aortic valve disease (stenosis, regurgitation). This automated quantitative signature exploits the entire 4D flow MRI velocity field information by encoding the distribution of the time-resolved flow co-disparities over the entire aorta to capture intrinsic patient-specific 4D hemodynamic properties.

Figure 6:
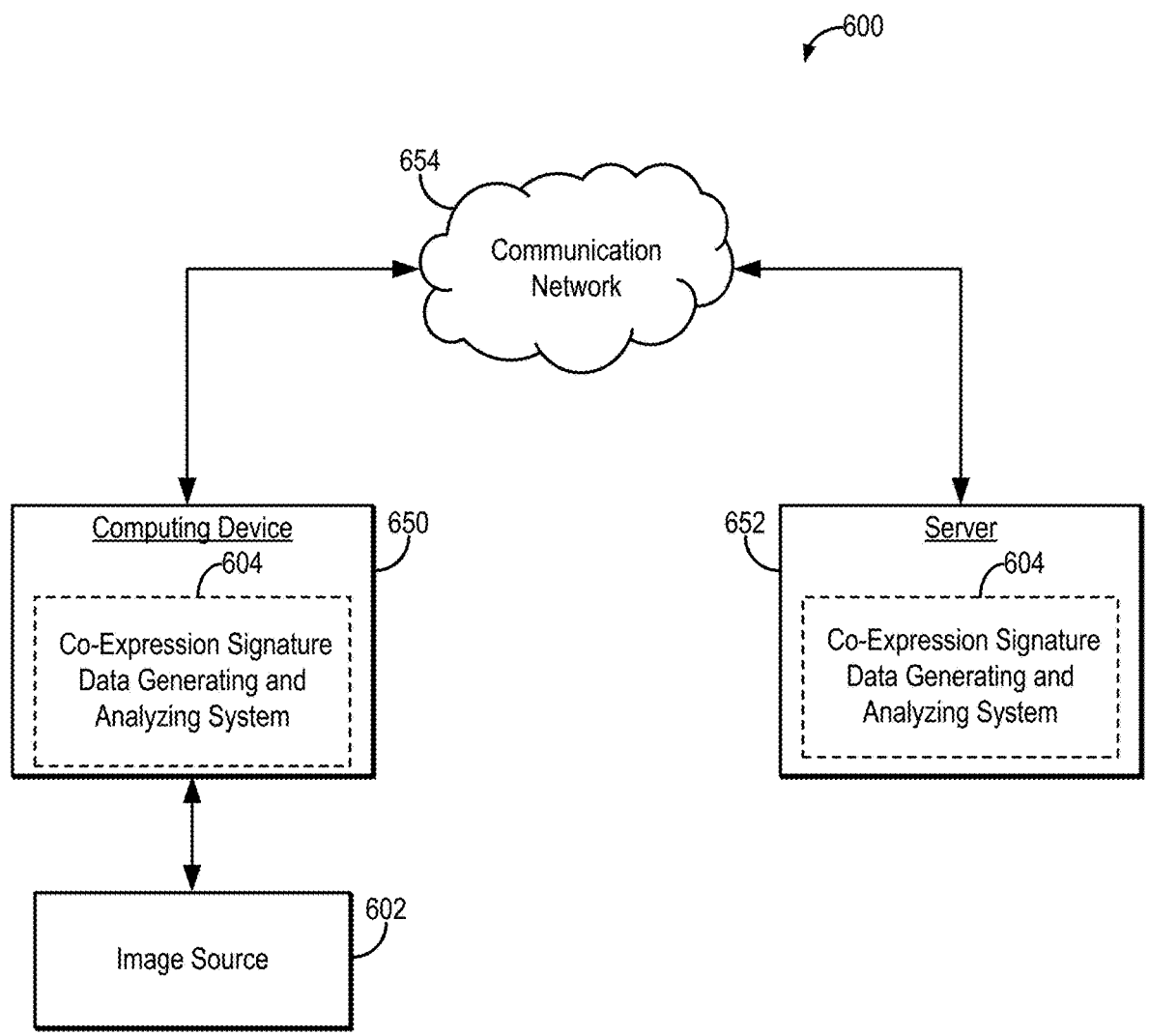
FIG. 6 shows an example of a system for co-expression signature data generating and analyzing in accordance with some embodiments of the systems and methods described in the present disclosure.

Referring now to FIG. 6, an example of a system 600 for co-expression signature data generating and analyzing in accordance with some embodiments of the systems and methods described in the present disclosure is shown. As shown in FIG. 6, a computing device 650 can receive one or more types of data (e.g., flow data or other data field data contained in or otherwise derived from imaging data) from image source 602, which may be an MRI image source as one non-limiting example. In some embodiments, computing device 650 can execute at least a portion of a co-expression signature data generating and analyzing system 604 to analyze from data received from the image source 602.

Additionally or alternatively, in some embodiments, the computing device 650 can communicate information about data received from the image source 602 to a server 652 over a communication network 654, which can execute at least a portion of the co-expression signature data generating and analyzing system 604 to analyze from data received from the image source 602. In such embodiments, the server 652 can return information to the computing device 650 (and/or any other suitable computing device) indicative of an output of the co-expression signature data generating and analyzing system 604 to analyze from data received from the image source 602.

In some embodiments, computing device 650 and/or server 652 can be any suitable computing device or combination of devices, such as a desktop computer, a laptop computer, a smartphone, a tablet computer, a wearable computer, a server computer, a virtual machine being executed by a physical computing device, and so on. The computing device 650 and/or server 652 can also reconstruct images from the data.

In some embodiments, image source 602 can be any suitable source of image data (e.g., measurement data, images reconstructed from measurement data), such as an MRI system, another computing device (e.g., a server storing image data), and so on. In some embodiments, image source 602 can be local to computing device 650. For example, image source 602 can be incorporated with computing device 650 (e.g., computing device 650 can be configured as part of a device for capturing, scanning, and/or storing images). As another example, image source 602 can be connected to computing device 650 by a cable, a direct wireless link, and so on. Additionally or alternatively, in some embodiments, image source 602 can be located locally and/or remotely from computing device 650, and can communicate data to computing device 650 (and/or server 652) via a communication network (e.g., communication network 654).

In some embodiments, communication network 654 can be any suitable communication network or combination of communication networks. For example, communication network 654 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 654 can be a local area network, a wide area network, a public network (e.g., the Internet), a private or semi-private network (e.g., a corporate or university intranet), any other suitable type of network, or any suitable combination of networks. Communications links shown in FIG. 6 can each be any suitable communications link or combination of communications links, such as wired links, fiber optic links, Wi-Fi links, Bluetooth links, cellular links, and so on.

Figure 7:
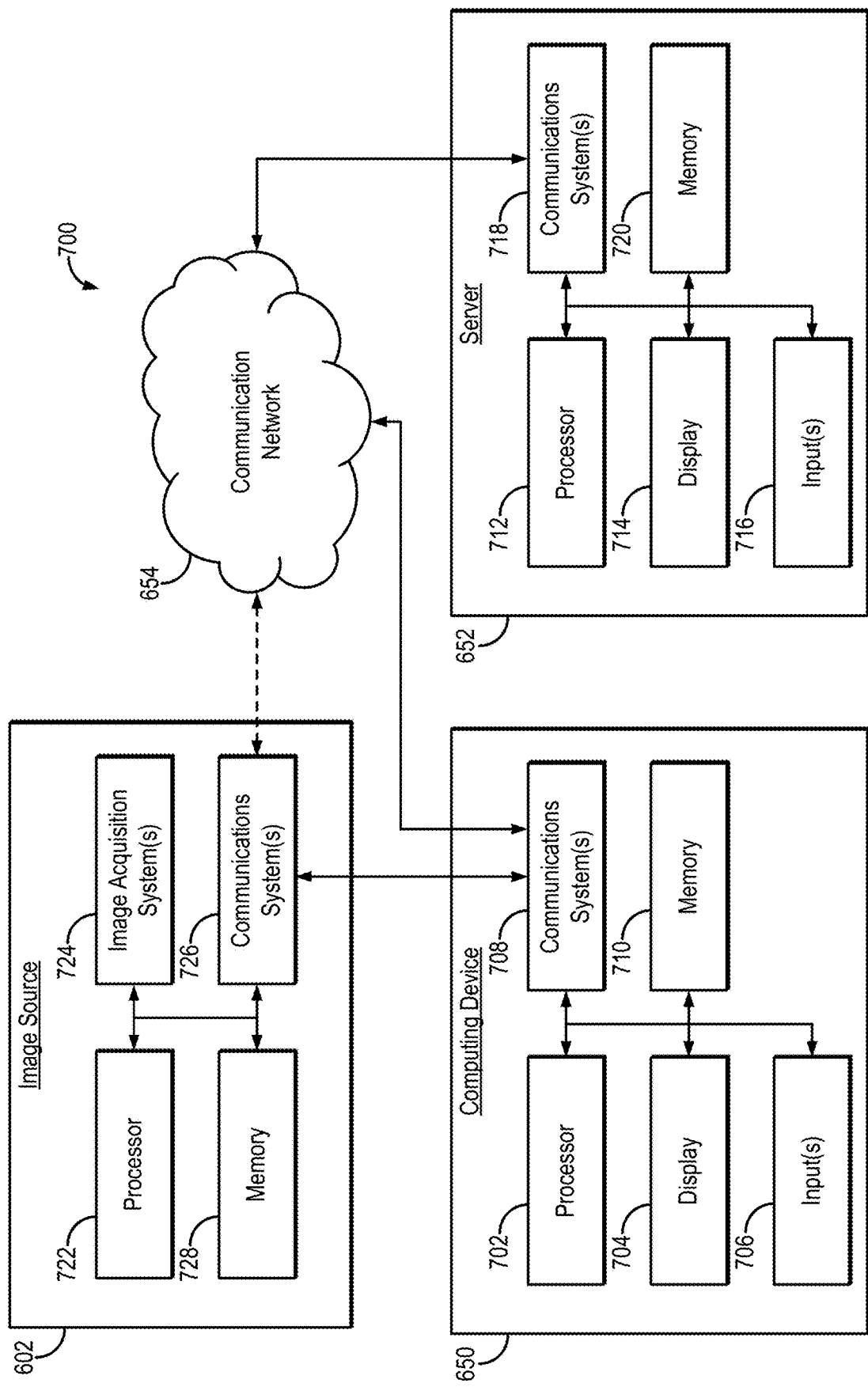
FIG. 7 shows an example of hardware that can be used to implement image source, computing device, and server in accordance with some embodiments of the systems and methods described in the present disclosure.

Referring now to FIG. 7, an example of hardware 700 that can be used to implement image source 602, computing device 650, and server 652 in accordance with some embodiments of the systems and methods described in the present disclosure is shown. As shown in FIG. 7, in some embodiments, computing device 650 can include a processor 702, a display 704, one or more inputs 706, one or more communication systems 708, and/or memory 710. In some embodiments, processor 702 can be any suitable hardware processor or combination of processors, such as a central processing unit ("CPU"), a graphics processing unit ("GPU"), and so on. In some embodiments, display 704 can include any suitable display devices, such as a computer monitor, a touchscreen, a television, and so on. In some embodiments, inputs 706 can include any suitable input devices and/or sensors that can be used to receive user input, such as a keyboard, a mouse, a touchscreen, a microphone, and so on.

In some embodiments, communications systems 708 can include any suitable hardware, firmware, and/or software for communicating information over communication network 654 and/or any other suitable communication networks. For example, communications systems 708 can include one or more transceivers, one or more communication chips and/or chip sets, and so on. In a more particular example, communications systems 708 can include hardware, firmware and/or software that can be used to establish a Wi-Fi connection, a Bluetooth connection, a cellular connection, an Ethernet connection, and so on.

In some embodiments, memory 710 can include any suitable storage device or devices that can be used to store instructions, values, data, or the like, that can be used, for example, by processor 702 to present content using display 704, to communicate with server 652 via communications system(s) 708, and so on. Memory 710 can include any suitable volatile memory, non-volatile memory, storage, or any suitable combination thereof. For example, memory 710 can include RAM, ROM, EEPROM, one or more flash drives, one or more hard disks, one or more solid state drives, one or more optical drives, and so on. In some embodiments, memory 710 can have encoded thereon, or otherwise stored therein, a computer program for controlling operation of computing device 650. In such embodiments, processor 702 can execute at least a portion of the computer program to present content (e.g., images, user interfaces, graphics, tables), receive content from server 652, transmit information to server 652, and so on.

In some embodiments, server 652 can include a processor 712, a display 714, one or more inputs 716, one or more communications systems 718, and/or memory 720. In some embodiments, processor 712 can be any suitable hardware processor or combination of processors, such as a CPU, a GPU, and so on. In some embodiments, display 714 can include any suitable display devices, such as a computer monitor, a touchscreen, a television, and so on. In some embodiments, inputs 716 can include any suitable input devices and/or sensors that can be used to receive user input, such as a keyboard, a mouse, a touchscreen, a microphone, and so on.

In some embodiments, communications systems 718 can include any suitable hardware, firmware, and/or software for communicating information over communication network 654 and/or any other suitable communication networks. For example, communications systems 718 can include one or more transceivers, one or more communication chips and/or chip sets, and so on. In a more particular example, communications systems 718 can include hardware, firmware and/or software that can be used to establish a Wi-Fi connection, a Bluetooth connection, a cellular connection, an Ethernet connection, and so on.

In some embodiments, memory 720 can include any suitable storage device or devices that can be used to store instructions, values, data, or the like, that can be used, for example, by processor 712 to present content using display 714, to communicate with one or more computing devices 650, and so on. Memory 720 can include any suitable volatile memory, non-volatile memory, storage, or any suitable combination thereof. For example, memory 720 can include RAM, ROM, EEPROM, one or more flash drives, one or more hard disks, one or more solid state drives, one or more optical drives, and so on. In some embodiments, memory 720 can have encoded thereon a server program for controlling operation of server 652. In such embodiments, processor 712 can execute at least a portion of the server program to transmit information and/or content (e.g., data, images, a user interface) to one or more computing devices 650, receive information and/or content from one or more computing devices 650, receive instructions from one or more devices (e.g., a personal computer, a laptop computer, a tablet computer, a smartphone), and so on.

In some embodiments, image source 602 can include a processor 722, one or more image acquisition systems 724, one or more communications systems 726, and/or memory 728. In some embodiments, processor 722 can be any suitable hardware processor or combination of processors, such as a CPU, a GPU, and so on. In some embodiments, the one or more image acquisition systems 724 are generally configured to acquire data, images, or both, and can include an MRI system Additionally or alternatively, in some embodiments, one or more image acquisition systems 724 can include any suitable hardware, firmware, and/or software for coupling to and/or controlling operations of an MRI system In some embodiments, one or more portions of the one or more image acquisition systems 724 can be removable and/or replaceable.

Note that, although not shown, image source 602 can include any suitable inputs and/or outputs. For example, image source 602 can include input devices and/or sensors that can be used to receive user input, such as a keyboard, a mouse, a touchscreen, a microphone, a trackpad, a trackball, and so on. As another example, image source 602 can include any suitable display devices, such as a computer monitor, a touchscreen, a television, etc., one or more speakers, and so on.

In some embodiments, communications systems 726 can include any suitable hardware, firmware, and/or software for communicating information to computing device 650 (and, in some embodiments, over communication network 654 and/or any other suitable communication networks). For example, communications systems 726 can include one or more transceivers, one or more communication chips and/or chip sets, and so on. In a more particular example, communications systems 726 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 728 can include any suitable storage device or devices that can be used to store instructions, values, data, or the like, that can be used, for example, by processor 722 to control the one or more image acquisition systems 724, and/or receive data from the one or more image acquisition systems 724; to images from data; present content (e.g., images, a user interface) using a display; communicate with one or more computing devices 650; and so on. Memory 728 can include any suitable volatile memory, non-volatile memory, storage, or any suitable combination thereof. For example, memory 728 can include RAM, ROM, EEPROM, one or more flash drives, one or more hard disks, one or more solid state drives, one or more optical drives, and so on. In some embodiments, memory 728 can have encoded thereon, or otherwise stored therein, a program for controlling operation of image source 602. In such embodiments, processor 722 can execute at least a portion of the program to generate images, transmit information and/or content (e.g., data, images) to one or more computing devices 650, receive information and/or content from one or more computing devices 650, receive instructions from one or more devices (e.g., a personal computer, a laptop computer, a tablet computer, a smartphone, etc.), and so on.

The present disclosure has described one or more preferred embodiments, and it should be appreciated that many equivalents, alternatives, variations, and modifications, aside from those expressly stated, are possible and within the scope of the invention.

The invention claimed is:

1. A method for generating co-expression signature data from data field data obtained from imaging data acquired with an imaging system, the method comprising:
   (a) accessing data field data comprising a plurality of voxels, wherein the data field data were obtained from imaging data acquired from a subject using an imaging system and each voxel in the data field data comprises data field component;
   (b) generating co-expression signature data from the data field data by:
      computing a similarity metric for each of a plurality of voxel pairs in the data field data, wherein the similarity metric indicates one of a similarity or disparity between the data field component in each voxel pair; and
      computing the co-expression signature data as a distribution of the similarity metrics;
   wherein the co-expression signature data encode a distribution of pairwise similarities or disparities in the data field data that are representative of at least one of physiological changes or structural changes in the subject.

2. The method as recited in claim 1, further comprising generating signature dissimilarity data by comparing the co-expression signature data with baseline data.

3. The method as recited in claim 2, wherein the co-expression signature data are compared with the baseline data by computing a distance metric between the co-expression signature data and the baseline data.

4. The method as recited in claim 3, wherein the distance metric is an earth mover's distance (EMD).

5. The method as recited in claim 2, wherein the baseline data includes data corresponding to other subjects.

6. The method as recited in claim 2, wherein the baseline data includes historical data corresponding to the subject.

7. The method as recited in claim 1, wherein step (b) includes segmenting the data field data to generate a vessel volume corresponding to a blood vessel in the subject, wherein the vessel volume comprises voxels associated with spatial locations in the blood vessel.

8. The method as recited in claim 1, wherein step (b) includes selecting the plurality of voxel pairs as a subset of the data field data.

9. The method as recited in claim 1, wherein step (b) includes performing stochastic discrete uniform random sampling in order to select the plurality of voxel pairs in the data field data.

10. The method as recited in claim 1, wherein step (b) includes selecting the plurality of voxel pairs as constituting all of the data field data.

11. The method as recited in claim 1, wherein step (b) includes defining one of a consistent time point or range of time points in a cardiac cycle at which to generate the co-expression signature data from data field data associated with that consistent time point or range of time points.

12. The method as recited in claim 1 further comprising outputting a report based on the similarity metric and the co-expression signature data to at least one of a memory or a display.

13. The method as recited in claim 1, wherein the data field data comprises flow data indicative of blood flow in a vasculature of the subject, and wherein each data field component comprises flow vector data.

14. The method as recited in claim 11, wherein the similarity metric is an angular similarity metric that indicates a similarity between flow vector data at each voxel in the pair of voxels.

15. The method as recited in claim 1, wherein the data field component comprises scalar field data.

16. The method as recited in claim 1, wherein the data field component comprises vector field data.

17. The method as recited in claim 1, wherein the data field component comprises tensor field data.

18. The method as recited in claim 1, wherein the imaging system is a magnetic resonance imaging (MRI) system.

19. The method as recited in claim 1, wherein the imaging data comprises first imaging data acquired with a first imaging system and second imaging data acquired with a second imaging system, and wherein the plurality of voxel pairs comprises voxels pairs composed of a first voxel from the first imaging data and a second voxel from the second imaging data.

20. The method as recited in claim 19, wherein the first imaging data were acquired at a first scale associated with a first spatial resolution and the second imaging data were acquired at a second scale associated with a second spatial resolution that is different from the first spatial resolution.

21. The method as recited in claim 19, wherein the first imaging system corresponds to a first imaging modality and the second imaging system corresponds to a second imaging modality that is different from the first imaging modality.

22. The method as recited in claim 1, wherein the distribution of the similarity metrics comprises a probability distribution function.

23. The method as recited in claim 22, wherein the probability distribution function comprises a probability density function.

24. A method for generating co-expression signature data from point-distributed data, the method comprising:
   (a) accessing point-distributed data comprising a plurality of data points, wherein each data point in the point-distributed data comprises an N-dimensional data field component;
   (b) generating co-expression signature data from the point-distributed data by:
      computing a similarity metric for each of a plurality of data point pairs in the point-distributed data, wherein the similarity metric indicates one of a similarity or disparity between the N-dimensional data field component in each data point pair; and
      computing the co-expression signature data as a distribution of the similarity metrics;
   wherein the co-expression signature data encode a distribution of pairwise similarities or disparities in the point-distributed data.

25. The method as recited in claim 24, wherein the point-distributed data comprise imaging data acquired with an imaging system.

26. The method as recited in claim 25, wherein the plurality of data point pairs comprises a plurality of voxel pairs.

27. The method as recited in claim 24, wherein the point-distributed data comprise biomedical data acquired with a biomedical measurement system.

28. The method as recited in claim 27, wherein the biomedical measurement system comprises an electrophysiology measurement system.

29. The method as recited in claim 24, wherein the distribution of the similarity metrics comprises a probability distribution.

30. The method as recited in claim 29, wherein the probability distribution comprises a probability density function.

* * * * *